United States Patent
Ganz (12)

(10) Patent No.: US 6,464,625 B2
(45) Date of Patent: Oct. 15, 2002

(54) THERAPEUTIC METHOD AND APPARATUS FOR DEBILITATING OR KILLING MICROORGANISMS WITHIN THE BODY

(76) Inventor: Robert A. Ganz, 1431 Lakeview Ave., Minneapolis, MN (US) 55416

( * ) Notice: Subject to any disclaimer, the term of this patent is extended or adjusted under 35 U.S.C. 154(b) by 0 days.

(21) Appl. No.: 09/338,687

(22) Filed: Jun. 23, 1999

(65) Prior Publication Data

US 2001/0049464 A1 Dec. 6, 2001

(51) Int. Cl.[7] .................................................. A61N 5/00
(52) U.S. Cl. ........................................................ 600/3
(58) Field of Search ......................... 607/88–94; 600/18

(56) References Cited

U.S. PATENT DOCUMENTS

| 2,173,258 A | 9/1939 | Lederer |
| 3,060,924 A | * 10/1962 | Crush ............................ 600/6 |
| 3,582,702 A | 6/1971 | Almer |
| 4,164,680 A | 8/1979 | Villalobos |
| 4,418,744 A | 12/1983 | Edelson |
| 4,683,889 A | 8/1987 | Edelson |

(List continued on next page.)

FOREIGN PATENT DOCUMENTS

| EP | 0 359 724 A2 | 3/1990 |
| EP | 0 359 724 A3 | 3/1990 |
| EP | 0572 770 A1 | 6/1993 |
| EP | 0 718 864 A1 | 6/1996 |
| EP | 0 860 180 A2 | 8/1998 |
| GB | 230 183 | 3/1925 |
| GB | 997 352 | 7/1965 |
| JP | 10-94583 | 4/1998 |
| WO | WO97/06549 | 2/1997 |
| WO | WO97/07740 | 3/1997 |

OTHER PUBLICATIONS

C.E. Millson et al., Ex–Vivo Treatment of Gastric Helico–bacter Infection by Photodynamic Therapy; Journal of Photo–chemistry and Photobiology B: Biology 32 (1996) 59–65 London.

C. E. Millson et al., The Killing of Helicobacter pylori by Low Power Laser Light in the Presence of a Photosensitizer; J Med Microbiology vol. 44, (1996) 245–252.

Martinetto P., et al. Bactericidal effects induced by laser irradiation and haematoporphyrin against gram–positive and gram–negative micro–orgamisms. *Drugs Exp. Clin Res.* XII (4): 335–342, 1986.

(List continued on next page.)

Primary Examiner—Samuel G. Gilbert
(74) Attorney, Agent, or Firm—James V. Harmon

(57) ABSTRACT

A treatment method and apparatus for debilitating or killing *Helicobacter pylori* or other microorganisms within the body of a patient is especially suited for treating stomach or duodenal ulcers. The present therapeutic method involves the use of ionizing radiation for eliminating pathogenic microorganisms within or supported upon the lining of a body cavity of a patient, e.g., the stomach. An elongated flexible shaft is provided for insertion into the body in any of various ways selected by the surgeon. It can be placed endoscopically, e.g., through the esophagus, placed surgically, placed laparoscopically or by CAT scan-guided percutaneous insertion. A radiant energy distribution head is provided at the end of the flexible shaft to transmit ionizing radiation for destroying microorganisms within the body. Radiant energy, e.g., x-ray, ultraviolet light, beta radiation, gamma radiation, radio waves, microwaves, or infrared energy, is then transferred from the head of the instrument to the epithelium around the head of the instrument in an amount sufficient to debilitate or kill the *Helicobacter pylori* or other microorganisms in the lining of the body cavity.

16 Claims, 5 Drawing Sheets

U.S. PATENT DOCUMENTS

| | | | |
|---|---|---|---|
| 4,830,460 A | * 5/1989 | Goldenberg | 350/96.26 |
| 4,987,007 A | 1/1991 | Wagal et al. | |
| 4,998,930 A | * 3/1991 | Lundahl | 606/15 |
| 5,090,043 A | 2/1992 | Parker et al. | |
| 5,153,900 A | 10/1992 | Nomikos et al. | |
| 5,282,781 A | * 2/1994 | Liprie | 600/3 |
| 5,334,171 A | 8/1994 | Kaldnay | |
| 5,354,293 A | * 10/1994 | Beyer et al. | 606/15 |
| 5,405,369 A | * 4/1995 | Selman et al. | 607/88 |
| 5,422,926 A | 6/1995 | Smith et al. | |
| 5,531,662 A | * 7/1996 | Carr | 600/2 |
| 5,566,221 A | 10/1996 | Smith et al. | |
| 5,591,199 A | 1/1997 | Porter et al. | |
| 5,621,780 A | 4/1997 | Smith et al. | |
| 5,653,683 A | * 8/1997 | D'Andrea | 604/21 |
| 5,748,699 A | 5/1998 | Smith | |
| 5,871,522 A | 2/1999 | Sentilles | |
| 5,910,102 A | * 6/1999 | Hastings | 600/3 |
| 6,026,331 A | * 2/2000 | Feldberg et al. | 607/102 |
| 6,083,148 A | * 7/2000 | Williams | 600/2 |
| 6,095,966 A | * 8/2000 | Chornenky et al. | 600/3 |

OTHER PUBLICATIONS

Kubey W., et al. In Vitro studies on the microbicidal effectiveness of a xenon–based ultraviolet light device for continuous ambulatory peritoneal connection. *Blood Purif.* 9 (2): 102–108, 1991.

U.S. patent application Ser. No. 09/027,010 filed Feb. 20, 1998 by Victor I. Chornenty, Michael R. Forman, and Robert A. Ganz: X–Ray, Device Having a Dilation Structure for Delivering Localized Radiation to an Interior of a Body.

* cited by examiner

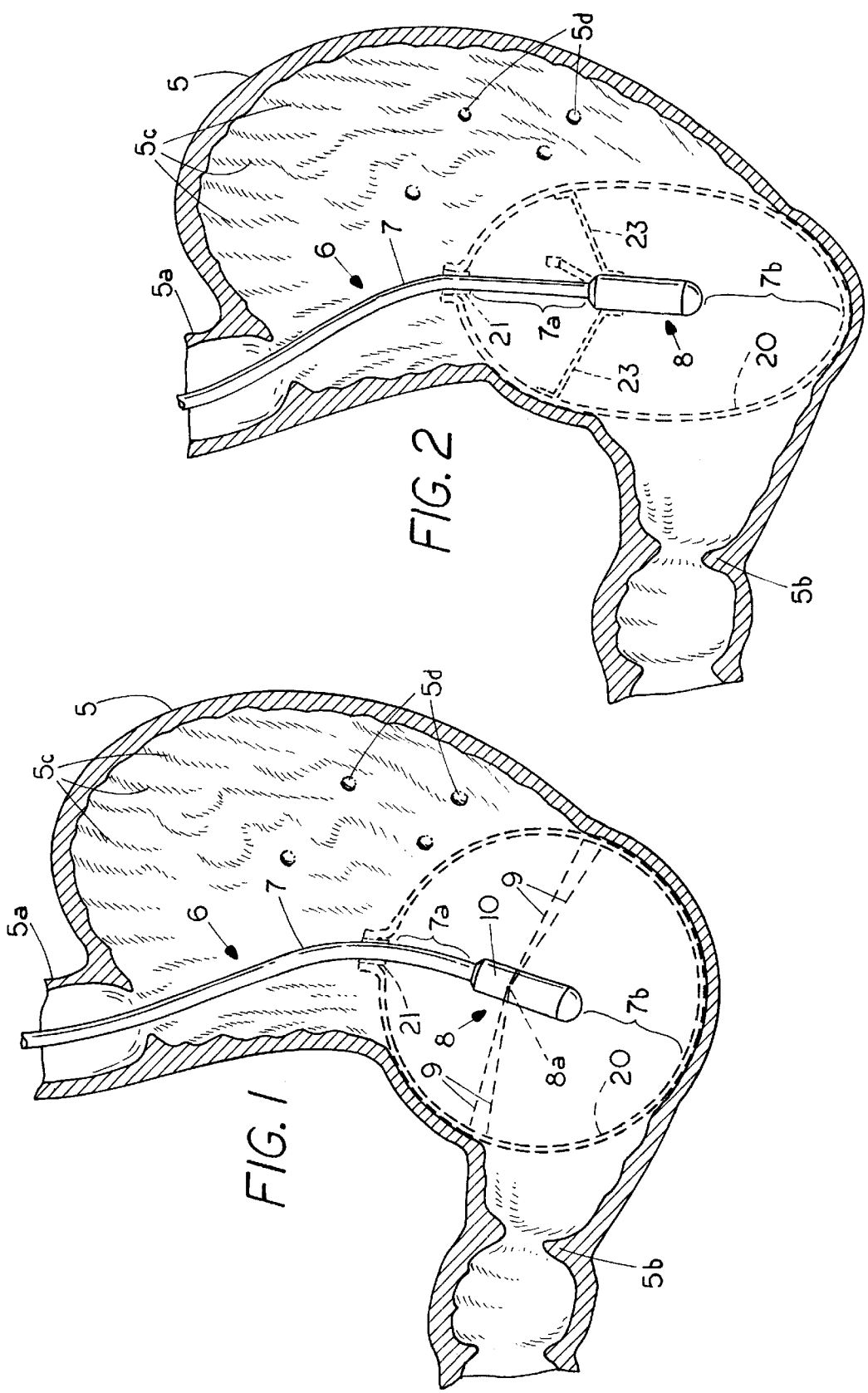

THERAPEUTIC METHOD AND APPARATUS FOR DEBILITATING OR KILLING MICROORGANISMS WITHIN THE BODY

FIELD OF THE INVENTION

This invention relates to a method and apparatus for the destruction of microorganisms on or within a body cavity of a patient through the use of ionizing radiation.

BACKGROUND OF THE INVENTION

Infections involving the human gastrointestinal tract are extremely common, involving many millions of people on an annual basis. These infections include bacteria, viruses, and fungi, and are responsible for significant illness, morbidity and, in many cases, death. While the invention has utility in destroying microorganisms in various parts of the body, e.g., the stomach, bowel, lungs, peritoneal cavity, urinary tract, etc., it is particularly useful in the treatment of gastrointestinal infections.

It has recently been shown that the most common gastrointestinal infection in the world is due to *Helicobacter pylori*, a bacterial pathogen that infects the stomach and duodenum. In the United States, for example, *Helicobacter pylori* is found in approximately 20% of the adult population. It is a chronic gut infection and, once acquired, is notoriously difficult to cure. Most infectious bacteria can be readily destroyed by the human immune system; however, *Helicobacter pylori* lives in the lumen of the stomach and on the surfaces of the stomach and duodenal cells, making it relatively resistant to a host immune response, even if vigorous. The present invention, however, takes advantage of its location in the treatment method and apparatus employed in the present invention.

*Helicobacter pylori* is typically a silent infection in humans, the majority of the time causing a relatively innocuous gastric inflammation or gastritis. In a significant minority of infected people, however, *Helicobacter pylori* can cause symptomatic gastritis, gastric ulcer, duodenal ulcer, gastric cancer, and gastric lymphoma. The organism is responsible for approximately 90% of all reported duodenal ulcers, 50% of gastric ulcers, 85% of gastric cancer, and virtually 100% of gastric lymphoma. Millions of Americans have symptomatic gastritis due to *Helicobacter pylori* or the much more serious entities noted above. *Helicobacter pylori* is responsible for thousands of deaths in this country due to complicated ulcer disease and cancer, and is considered to be a Class 3 carcinogen by the World Health Organization, in the same class as Benzene and DDT.

The organism is found in all countries in the world, causing the same symptoms, diseases, and deaths, but it is most prevalent in undeveloped countries, presumably due to poor hygiene, contaminated water supplies and crowding. In Peru and other South American countries, for example, the prevalence rate of *Helicobacter pylori* infection approaches 90%.

There is no vaccine available for *Helicobacter pylori* and none is anticipated in the foreseeable future, despite years of intensive effort. The only treatment currently available is prolonged and complicated antibiotic regimens involving three or four expensive antibiotics given over a two-week period. Even using a vigorous antibiotic regimen, however, up to 20% of those treated are not cured of their infection. The antibiotics used are powerful, sometimes not well tolerated, and can cause nausea, an altered taste sensation and diarrhea. Allergic reactions are not uncommon. In addition to the problems of efficacy and side effects, antibiotic resistance to this organism is growing rapidly. Up to 50% of the Helicobacter isolates are now resistant to one or more of the best antibiotics known to cure the infection. This problem of antibiotic resistance is only expected to grow in the future, leading to worsening disease outcomes and an ever-increasing health expense.

Thus, a great need exists for a new, effective, rapid and well-tolerated cure of *Helicobacter pylori*, a luminal infection of the gut. There also exists a need for a well-tolerated and effective treatment for debilitating or killing microorganisms with as little intrusion as possible in other body cavities, such as the bowel, lungs, peritoneal cavity or urinary tract.

SUMMARY OF THE INVENTION

This invention provides a treatment method and apparatus for debilitating or killing *Helicobacter pylori* or other microorganisms within the body of a patient and is especially suited for treating stomach or duodenal ulcers. The present therapeutic method involves the use of ionizing radiation for eliminating pathogenic microorganisms within or supported upon the lining of a body cavity of a patient, e.g., the stomach. An elongated flexible shaft is provided for insertion into the body in any of various ways selected by the surgeon. It can be placed endoscopically, e.g., through the esophagus, placed surgically, placed laparoscopically or by CAT scan-guided percutaneous insertion. A radiant energy distribution head is provided at the end of the flexible shaft to provide ionizing radiation for destroying microorganisms within the body. Radiant energy, e.g., x-ray, ultraviolet light, beta radiation, gamma radiation, radio waves, microwaves, or infrared energy is then transferred from the head of the instrument to the epithelium around the head of the instrument in an amount sufficient to debilitate or kill the *Helicobacter pylori* or other microorganisms in the lining of the body cavity.

In one preferred form of instrument, the flexible shaft comprises a coaxial cable surrounded by an electrical insulation layer and has the radiant energy distribution head located at its distal end. In a preferred optional form of the invention, a positioning and distending device around the head of the instrument is of sufficient size to contact and expand the walls of the body cavity in which it is placed both in the front of the distribution head as well as on the sides of the distribution head. For example, the head of the instrument can be supported a controlled distance from the wall of the body cavity by an expandable balloon so as to regulate the amount of energy transferred to the microorganisms. The balloon is preferably bonded to a portion of the flexible shaft at a point spaced from the head. The ionizing radiation can be x-ray energy, infrared, ultraviolet, radio waves, microwave, beta radiation or gamma radiation. Other forms of ionizing radiant energy that can be used for killing or debilitating surface microorganisms will be apparent to those skilled in the art once the present specification has been read and understood.

These and other more detailed and specific objects of the present invention will be better understood by reference to the following figures and detailed description which illustrate by way of example of but a few of the various forms of the invention within the scope of the appended claims.

THE FIGURES

FIG. 1 is a vertical cross-sectional view showing the use of the invention in the stomach.

FIG. 2 is a view similar to FIG. 1 showing an elliptical balloon in use for positioning an ionizing radiation source in the stomach.

DETAILED DESCRIPTION OF THE INVENTION

Figure 3:
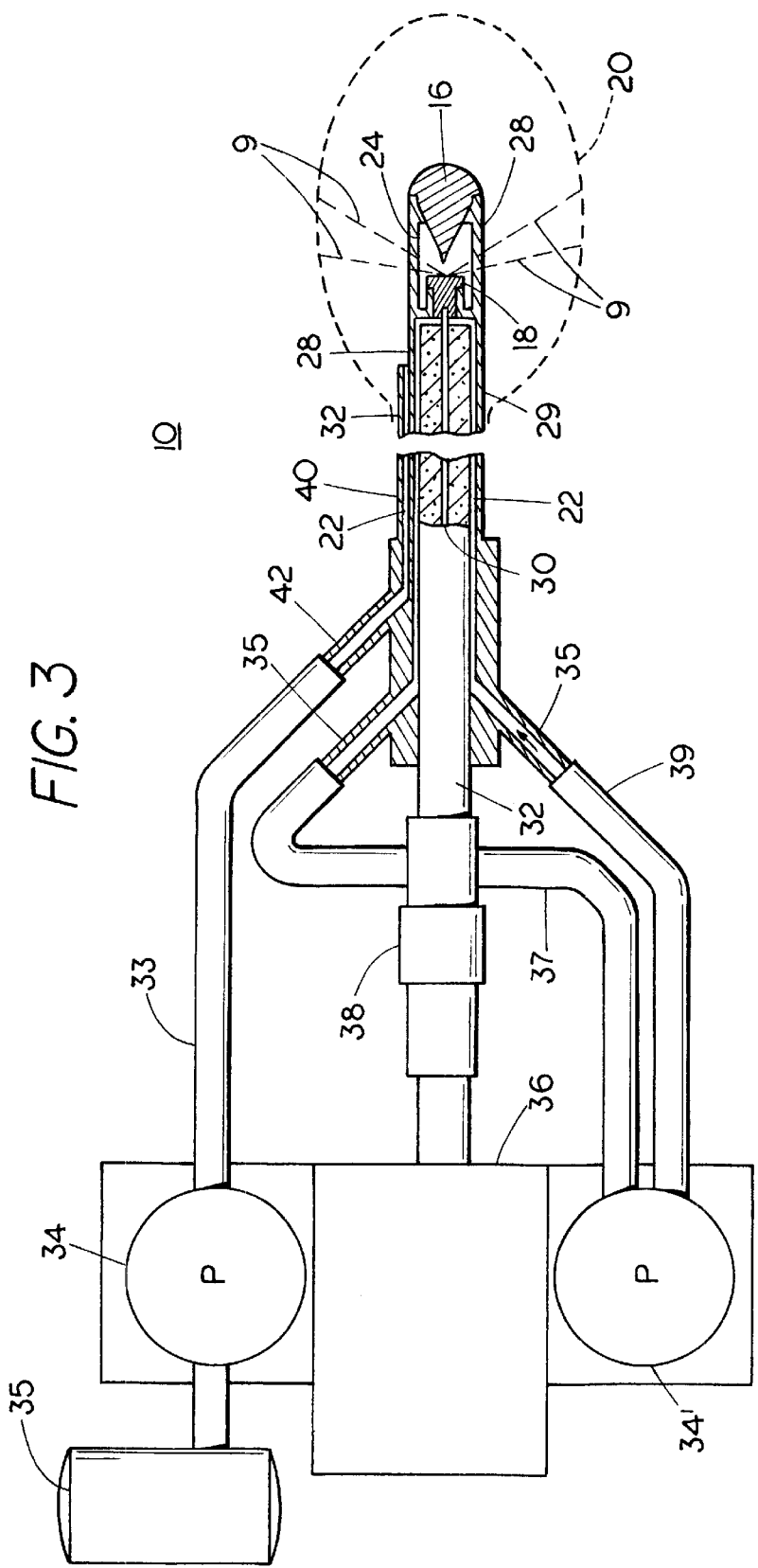
FIG. 3 is a diagrammatic, longitudinal, cross-sectional view of an instrument and supporting equipment in accordance with one form of the invention.

The therapeutic method in accordance with the present invention is suited for use in various body cavities including, but not limited to, the stomach, the bowel, the lungs, the peritoneal cavity, the urinary tract, and can also be used with various devices, fabrication methods, arrangements, systems and methods of employment which irradiate the walls of various body cavities or interior sites within the body of a patient by means of ionizing radiation in sufficient amount to debilitate or kill microorganisms lining the body cavity in which the invention is used.

In one preferred form of the invention, an x-ray device is provided which includes components for producing localized x-ray radiation within a vacuum housing or tube and, optionally, including an inflatable balloon surrounding the vacuum housing and preferably connected near the distal end of the device for positioning the source of ionizing radiation as well as for expanding the walls of the body cavity. While the invention can be employed for killing or debilitating various pathogenic microorganisms, it can be used to advantage in treating *Helicobacter pylori* infections of the gastrointestinal system and other ailments in which ionizing radiation is to be delivered to portions of the body that are not easily accessible. In order to provide a better understanding, the present invention will be described by way of example in the treatment of *Helicobacter pylori* infections within the stomach. It should be understood, however, that the invention is not limited to specific apparatus or methods described.

*Helicobacter pylori* is an infection of the stomach and duodenum and the major cause of stomach ulcers. Various forms of ionizing radiation, including x-rays, radiation from isotopes, radio waves, microwaves, or light radiation, e.g., ultraviolet light in accordance with the invention provide an advantageous method of treating such infections. The x-ray device, for example, produces ionizing radiation that penetrates the lining of the body cavity, in this case the columnar epithelial lining of the walls of the stomach, or the epithelium of any other passage or lumen that is being treated. During this treatment, the ionizing radiation produces apoptosis or programmed cell death in which the DNA of the microorganism is rendered unable to divide. The apoptosis that occurs in the microorganisms is different from necrosis, another type of cell death. In apoptosis produced by the ionizing radiation, a disruption of the gene structure of the microorganism prevents it from further replication. Consequently, the microorganisms die by mutation and, in some cases, by the disruption of metabolic processes at the cellular level. Some fraction of the microorganisms may also be killed immediately by the radiation. An important advantage of the invention lies in the fact that many organisms, such as bacteria, are exquisitely sensitive to ionizing radiation, sensitive to a much greater degree than the surrounding human cells. Accordingly, the bacteria can be killed or debilitated by apoptosis without serious destruction of the host cells.

In one aspect of the present invention, a source of ionizing radiation such as an x-ray device is positioned in a body cavity, e.g., the stomach, for treating *H. pylori* infections by inducing apoptosis in the bacterial cells carried on or within in the epithelium lining the stomach. The x-ray or other ionizing radiation of the present invention can therefore be used to prevent the escalation of the infection to stomach ulcers and cancer.

Refer now to the figures wherein the same numbers refer to corresponding parts in the several views. FIGS. 1–4 illustrate by way of example one method of use in accordance with the present invention; the treatment of *Helicobacter pylori* infections of the stomach designated by the numeral 5. Numeral 5a indicates the esophagus and numeral 5b indicates the pyloric sphincter. In this case, an instrument 6 is provided which includes a flexible supporting cable or shaft 7 and a distal ionizing radiation distribution head 8 from which radiation emanates as shown by rays 9 that strike the adjacent lining of the stomach where the *H. pylori* infection thrives in the epithelium and mucous lining the stomach 5. In this case, the source of ionizing radiation is an x-ray device 10 that includes a cathode 16, an anode 18, and a getter 24, all disposed within a vacuum chamber or tube wall 28 (see especially FIGS. 3 and 4). The cable or shaft 7 permits a physician to maneuver the x-ray device 10 to the treatment site in the body. It is contemplated that different types of maneuvering devices could be employed to position the head 8 containing the x-ray device 10 which provides the ionizing radiation, depending upon the particular site to be treated. In the embodiments showing the use of the instrument 6 in the stomach and gastrointestinal system, it is helpful for the shaft 7 to be flexible, to have a reduced diameter and rounded forward end such that it can be easily introduced into the esophagus and stomach, either by itself or, if desired, through an appropriate flexible endoscope (not shown). In one particular embodiment, the shaft 7 will have an outer diameter of less than or equal to approximately 3 mm, allowing it to fit easily within a standard endoscope that typically has a working lumen diameter of about 3 mm. In other applications, the properties and dimensions of the shaft 7 may vary to meet the requirements of the task.

For many disorders, an annular or donut-shaped radiation pattern 9 is ideally suited for treatment. In order to achieve this pattern, many passages and other interior portions of the body need to be dilated while treatment is carried out with ionizing radiation from the x-ray device 10. The stomach is very soft and, except after a meal, is in a collapsed state. Rugae or folds 5c are present on its inner walls. Stomach ulcers resulting from an *H. pylori* infection are shown at 5d. In one preferred embodiment of the present invention an optional dilating balloon 20 can be provided, if desired, to dilate the passage of the body, such as the stomach, and thereby distend the stomach wall and hence spread the rugae 5c apart and thus flatten the stomach wall so that a uniform annular radiation pattern can be created. The balloon 20 can also be important in positioning and holding the distribution head 8 in the desired location, especially in a central position that is equidistant from all parts of the surrounding stomach wall so as to provide the same dose of radiation to all portions of the stomach 5 surrounding the distribution head 8.

When using a small x-ray emitter, a problem is sometimes encountered when too much heat is produced at the anode during operation. If water circulates through the balloon interior, it further serves to cool the x-ray emitter and dissipate the potentially damaging heat. If desired, the balloon 20 can be in fluid communication with a fluid loop 22 that is disposed within the shaft 7 to carry fluid from outside the body to the interior of the balloon 20, and provide a return path for the fluid. If desired, the fluid in loop 22 can circulate in the interior of the balloon 20, inflating the balloon 20, and can then be returned to the proximal portion of the shaft 7 through the fluid loop 22. A circulating pump 34 can be used to circulate the fluid and maintain the pressure required to achieve the desired balloon size. The pump 34 can be coupled to the fluid loop 22 via fluid ports 35. Other methods and devices known in the art may also be used to circulate the fluid and inflate the balloon 20.

Figure 4:
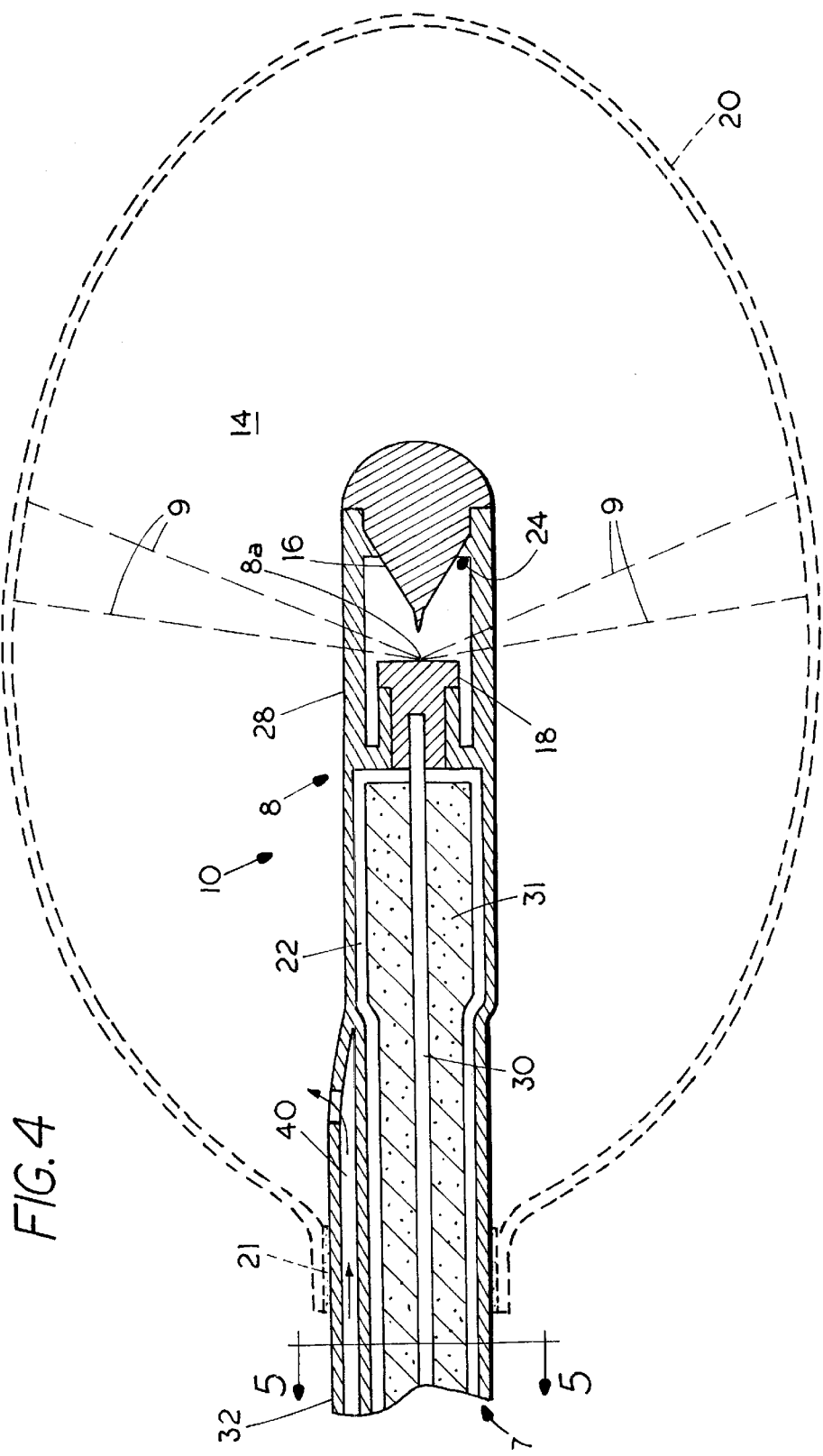
FIG. 4 is an enlarged longitudinal cross-sectional view of the distal end of an instrument in accordance with one form of the invention.
Figure 5:
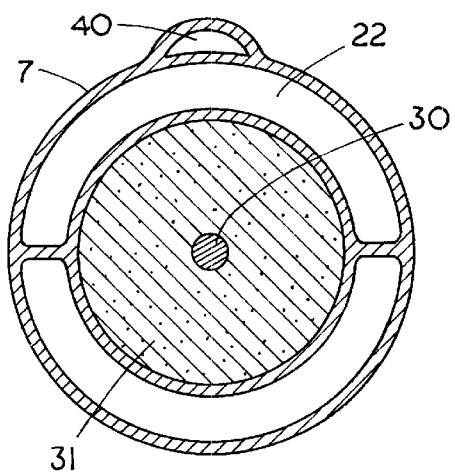
FIG. 5 is a vertical cross-sectional view taken on line 5—5 of FIG. 4.

Since it is generally desirable to provide independent control of the balloon size and cooling rate, a separate inflation lumen 40 and port 42 are shown in FIGS. 3 and 4 in fluid communication with the balloon 20. The fluid loop 22 is positioned to circulate cooling fluid in heat conducting relationship with the anode 18. In the embodiment shown in FIG. 3, the fluid loop 22 extends to surround a portion of the anode 18. The circulating action of the fluid loop 22 can thus provide a constant cooling rate, regardless of the extent of balloon dilation. The separate inflation lumen 40 can be coupled to a fluid source of adjustable pressure for the balloon 20 via the inflation port 42. In one embodiment, the fluid loop 22 and the inflation lumen 40 are created using plastic extrusion techniques. This arrangement has the advantage of allowing a liquid, e.g., water, to be used in fluid loop 22 for cooling and a gas, e.g., air, to be used for balloon inflation via lumen 40 so that the radiation from head 8 is not absorbed before reaching the stomach wall. Different cooling mechanisms could also be used.

Thus, during use, an inflation fluid is provided to expand the balloon 20 via lumen 40, inflation port 42 and a line 33 which is connected to the pump 34. If a liquid is used instead of a gas such as air, the liquid, e.g., water or saline, can be supplied from tank 35 which is connected to the inlet of pump 34. A gas is, however, preferred for filling the balloon 20, since it will have a negligible tendency to attenuate the radiation 9 emitted from the energy supply head 8. The coolant is circulated separately through the fluid loop 22 via lines 37 and 39 by means of circulating pump 34'. The pumps 34 and 34' are controlled by the power supply 36 which also supplies the high voltage current through the coaxial cable via coupling 38 to a cathode 16 and an anode 18 that are contained within a vacuum tube or chamber 28. The power supply 36 also includes an x-ray detector of suitable known construction that is used to calibrate the output of the device and control dosimetry, as well as an electronic display, if desired, for monitoring the therapy.

In order to apply an electrical field across the anode 18 and cathode 16, the anode 18 and cathode 16 are coupled to the power supply or high voltage source 36. In this embodiment, a coaxial cable is disposed within the flexible shaft 7 and coupled to the high voltage source 36 at the proximal end of the shaft 7. An internal conductor 30 of the coaxial cable is coupled to the anode 18 at the appropriate voltage and is enclosed in an insulating layer 31. An external conductive layer 32 of the coaxial cable is held at ground and coupled to cathode 16. A conductive solder on the outside of the vacuum chamber wall 28 may be used to couple the cathode 16 to the external conductive layer 32. Other known methods may also be used to apply an electric potential across the anode and cathode.

The vacuum tube 28 containing the cathode 16 and anode 18 can be of the thermionic type, with x-ray energies of, say, 8 KeV to 20 KeV. The tube can be powered to utilize 3 watts or less to produce soft x-ray radiation. A typical treatment time at 3 watts is about one to 20 minutes. When the prescribed dose of ionizing radiation has been delivered, the x-ray tube is turned off and the x-ray distribution head 8 is removed. When a radioactive isotope source is used instead of an x-ray source, the tissue is exposed to ionizing radiation for a few minutes, usually from about 15 minutes to 30 minutes.

The stomach in its relaxed state has a diameter of about 5–6 centimeters and cannot accommodate a rigid structure. In one embodiment, the device of the present invention can be inserted by being passed through a standard flexible laryngoscope or endoscope (not shown) that has a working lumen about 3 millimeters in diameter. Therefore, a coaxial cable used in this device must have a diameter small enough to be accommodated within the passage to be treated or within the scope-device used, and it must be able to carry the required voltages and have sufficient flexibility to make turns as it follows the passage. A diameter of less than or equal to 3 millimeters may be used for most applications. Standard high voltage coaxial cables are generally not flexible enough. Miniature high frequency coaxial cables are available with an outer diameter of approximately 1.0 mm to 3.0 mm which also exhibit sufficient flexibility and can carry the required voltage without breakdown. In one embodiment of the invention, a cable with an outer diameter of less than or equal to about 3 mm is used. Cables approximately 1–2 mm in diameter are also available, and are used in other embodiments. Such cables are manufactured by, for example, New England Electric Wire Corporation, Lisborn, N.H.

In one embodiment, a getter 24 is disposed within the vacuum housing 28 in order to aid in creating and maintaining a vacuum condition of high quality. The getter 24 has an activation temperature at which it will react with stray gas molecules in the vacuum. After the vacuum housing is assembled under vacuum conditions and the housing pumped out or baked out, the device is heated to the activation temperature and maintained at that temperature for several hours. It is desirable that the getter used have an activation temperature that is not so high that the x-ray device will be damaged with heated to the activation temperature. An SAES ST 101 alloy getter may be used, which has an activation temperature in the range of 750° C. to 900° C. and is composed of approximately 64% zirconium and 16% aluminum. An ST 707 alloy getter also may be used, which has an activation temperature in the range of 300° C. to 500° C. and is composed of approximately 70% zirconium, 18.6% vanadium, and 5.4% iron. Other suitable getters such as alkali metals can be used, if desired.

In order to most effectively decelerate the electrons striking the anode, a heavy metal material such as tungsten or gold can be used for the anode 18. The cathode and anode will be shaped to produce the desired radiation pattern. In the embodiment of FIGS. 1 and 2, the anode 18 is cylindrically shaped with a flat, circular side disposed toward the cathode 16, and the edge is rounded. The cathode 16 of this embodiment is cone-shaped.

A wall of the vacuum chamber 28 should be transparent to x-rays in order to allow the full dosage to reach the wall of the body cavity being treated. The wall 28 can comprise pyrolytic boron nitride, or another metal or ceramic material which is transparent to x-rays. Other possibilities include beryllium, beryllium oxide, aluminum, aluminum oxide, or graphite. In one embodiment, the outer diameter of the x-ray device is sized as large as, say, 1 centimeter to deliver the localized radiation to the interior of the stomach. In another embodiment, the outer diameter of the x-ray device is less than or equal to about three millimeters.

In some applications, such as use in the stomach, the diameter of the dilated balloon 20 should be able to vary with the pressure applied, so that the diameter of the balloon can be adjusted to fit the size of the patient's stomach or other passage. Therefore, an elastic balloon is particularly suited to gastric applications, where the elastic material will conform to the many surface features of the stomach and dilate the stomach more completely. However, in other applications, it may be desirable to employ an inelastic balloon with a fixed dilated diameter. It should be noted in FIG. 1 that the balloon 20, when present, is preferably secured to the flexible shaft 7, e.g. by means of a suitable adhesive 21 at a distance 7a from the radiation source 8a and also spaced from the radiation head 8. The distal end of the balloon 20 is free rather than being connected to the distribution head 8 or to anything else and is spaced from the source 8a of radiation by a distance 7b that is equal to 7a. The distances 7a and 7b each equals the approximate radius of the balloon 20 so as to locate the source 8a of the radiation 9 at the center of balloon 20, thus equalizing radiation flux in all directions. A round balloon is shown in FIG. 1.

In the x-ray device, an electric field exists at the cathode 16, while on the outside of the vacuum housing a conductive braid or solder is held at ground. These two potentials can be insulated from each other to reduce the chance of electrical flashover. A vacuum tube wall of pyrolytic boron nitride can provide some insulation. If a metal is used as the wall of the vacuum chamber 28, an insulating layer is beneficial to decrease the chance of electrical flashover. As additional protection against electrical flashover, an electrically insulating material can be placed at the joints on the outside of the vacuum chamber wall 28. The insulating material could be a potting compound, an injection-molded polymer, and other materials with electrically insulating properties. The vacuum chamber further includes a biocompatible outer coating, such as polyethylene or Teflon® material. The joints between the vacuum chamber wall 28 and the anode 18 may be vacuum furnace brazed, or may be sealed by conventional crimping methods.

The cathode 16 of the present invention consists of a material which displays emission characteristics when an electrical field is applied. One possible cathode material is a thin diamond film, which can be formed using conventional chemical vapor deposition techniques. A diamond film also may be formed using a laser ion source as described in U.S. Pat. No. 4,987,007 to Wagal, the contents of which are incorporated herein by reference. A graphite target and the substrate to be coated are disposed in a vacuum chamber. Between the two is an accelerating grid held at a high negative potential. The graphite target is radiated with a focused laser beam from a pulse laser. The laser beam ejects a plume of carbon vapor from the graphite target. A portion of the atoms in the plume are ionized by the focused laser beam, and the positive carbon ions are accelerated towards the substrate by the accelerating grid.

One possible cathode material is described in U.S. Patent Application entitled "DEVICE FOR DELIVERING LOCALIZED X-RAY RADIATION TO AN INTERIOR OF A BODY AND METHOD OF MANUFACTURE", the contents of which are incorporated herein by reference. The cathode material is a coating of carbon having diamond-like bonds which demonstrate negative electron affinity. It is also desirable to have sufficient conductivity to create a constant supply of electrons to the surface of the cathode. The presence of some graphite bonds in the diamond film will contribute to conductivity. Thus, a combination of a diamond film having both sp3 carbon bonds, to function as a cathode, and some sp2 carbon bonds, to facilitate conductivity, is particularly suited for use in many applications. Other elements may also be present in the film in small quantities. The diamond film will have the property that it can emit electrons at electrical fields greater than or equal to about 20 KV/micron. This required electric field is significantly lower when compared to that required for metal emitters such a molybdenum or silicon, which require greater than 1,000 KV/micron. If desired, the x-ray device and method can be constructed as described in U.S. Pat. No. 6,095,966 (in which I am a co-inventor) and is incorporated herein by reference.

When used to radiate the walls of an interior passage of the body, according to one embodiment of the invention, the x-ray device may be placed within a standard endoscope or laryngoscope. The x-ray device or other ionizing radiation described herein is introduced into the passage to be treated. The x-ray device, etc., is then guided through the passage, using techniques known in the art, until it is positioned near the area to be irradiated. The site to be irradiated may be viewed through the endoscope, and the area around the device may be flushed using the endoscope, if necessary. The dilating balloon 20 is then inflated by fluid, either liquid or gas, from the fluid pump to the desired diameter to expand the body cavity, in this case the stomach so as to hold the radiation distribution head 8 in the desired location and spread the rugae 5c apart so as to thereby flatten the stomach wall to insure uniform irradiation.

During operation, the high voltage generator is activated and an electrical field is established across the cathode 16 and the anode 18. The cathode 16 emits electrons which are accelerated toward the anode 18. As the electrons are decelerated by the anode 18, electromagnetic ionizing radiation is emitted. In this manner, x-ray radiation is produced by the Bremsstrahlung effect. As the x-ray radiation impinges upon the wall of the body cavity, such as the stomach, the *H. pylori* living on the surface of the passage are killed or debilitated by apoptosis as discussed above. In *H. pylori* infections, for example, the apoptosis eliminates the bacterial cells and reduces inflammation as well as the biochemical results of inflammation, thereby preventing ulcers, gastritis and cancer. When the desired dosage has been delivered, the voltage source is turned off and the balloon 20, when present, is deflated. The device is then withdrawn from the body.

The dosage of x-ray radiation to be applied to the interior of a body will generally be within the scope of the attending physician's judgment and will be based on individual conditions, such as the severity of the infection and the damage that has occurred at the site to be treated and the particular patient. In order to treat *H. pylori,* only the surface of the epithelium needs to be irradiated.

According to the present invention, x-ray radiation typically in the range of 0.1 to 50 Grays, and most preferably 1–2 Grays, may be applied. The treatment is typically structured to last about 2 to 10 minutes, and most preferably, 3 to 5 minutes. The x-ray emitter may be repositioned by moving it from one part of the stomach to another, either continuously or intermittently during the course of radiation treatment, depending on the length of the area requiring treatment.

It will be noted that because the source of radiation in the distribution head 8 is at the center of the balloon 20, all of the rays 9 will be of the same length when they strike the microorganisms, thereby assuring uniform radiation flux and, consequently, uniform exposure to radiation wherever the radiation strikes the wall of the cavity that is being treated. Uniform radiation exposure is also aided through the flattening of the stomach wall that is accomplished by the expansion of the balloon 20. The expanded balloon 20 also locks or wedges the radiation-supplying head 8 in place within the stomach 5, so that stomach contractions, which take place normally, cannot displace the instrument 6. During use, the balloon 20 should not be expanded to the point where the blood supply to the epithelium lining the stomach is cut off, since oxygen is necessary in forming free radicals which are important in the destruction of the microorganisms.

Refer now to FIG. 2 which illustrates a positioning balloon 20 of a different shape. In this case, the balloon 20 is generally elliptical in shape and is secured as already described in FIG. 1 by means of adhesive 21 at a distance 7a from the energy-supplying head 8, the space 7a being a substantial distance that is determined so as to place the energy distribution head 8 in approximately the center of the elliptically-shaped balloon 20. The axis of the ellipse is aligned with the distribution head 8. If desired, in order to prevent the head 8 from dangling away from the center of the balloon 20, optional radially extending tethers 23 that serve as positioning ligaments can be bonded at each end to extend between the distribution head 8 and the wall of the balloon 20. The tethers 23 can be formed from short lengths of cord, tape or narrow strips of cloth, etc. Other positioning means for locating the head 8 at the center of the balloon 20 will be apparent to those skilled in the art. The tethers 23 can be attached to the balloon 20 by adhesive during assembly while the balloon is enverted, i.e., inside out over the distal end of the distribution head 8.

Figure 6:
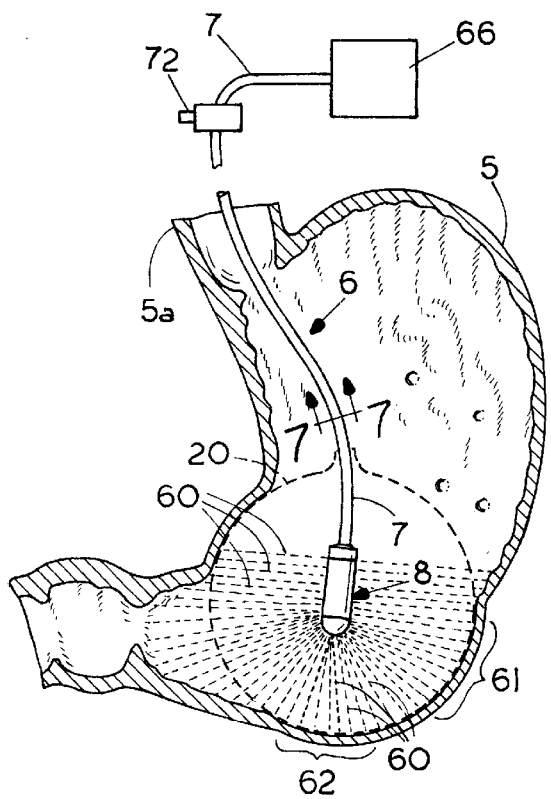
FIG. 6 is a vertical cross-sectional view of another form of the invention shown as it appears during use in the stomach.
Figure 7:
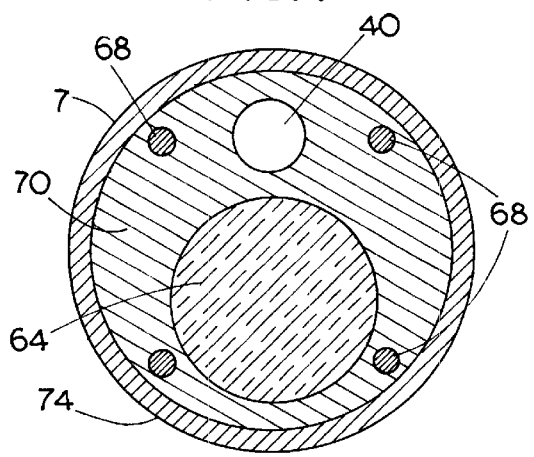
FIG. 7 is a transverse cross-sectional view taken on line 7—7 of FIG. 6 but on a larger scale.

Refer now to FIGS. 6 and 7 illustrating a modified form of the invention in which the same numerals refer to corresponding parts already described. In this case, ultraviolet light rays 60 are provided by the energy distribution head 8 which is formed from a transparent material, e.g., glass or fused quartz. The ultraviolet light 60 is projected both laterally at 61 as well as passing forwardly at 62 through the balloon 20 striking the wall of the stomach 5. The balloon 20 holds the radiant energy distribution head 8 in the desired position and also distends the wall of the stomach 5 so as to spread out the rugae 5c and thereby allow uniform exposure of the portion of the wall of the stomach that is being treated. As the ultraviolet light rays 60 strike the columnar epithelium lining the stomach, the H. pylori infecting the cells is killed or debilitated. The part of the stomach exposed to the ultraviolet light rays 60 can be changed by the physician, either by moving the balloon 20 and head 8 along the length of the stomach 5 toward the esophagus 5a or by changing the angle of the head 8 with respect to the longitudinal axis of the stomach 5 as will be described more fully below. The position of the instrument can also be confirmed using fluoroscopy or a CAT scan, if desired.

In this case, the cathode 16 and anode 18, as well as the conductor 30, are eliminated and replaced by a fiber optic bundle 64 (FIG. 7) which extends from a light source 66 (FIG. 6) through the entire length of the flexible shaft 7 via the esophagus 5a into the stomach 5, so as to carry ultraviolet light from the source 66 through the distribution head 8 to a light reflector or diffuser, e.g., of conical shape, inside the distribution head 8 which spreads the ultraviolet light rays 60 so that they pass through the balloon 20, striking the wall of the stomach 5 to the side and in front of the distribution head 8. As shown in FIG. 7, the inflation fluid for the balloon 20 is supplied through a lumen 40 as already described. The flexible shaft 7 can be provided with a plurality of longitudinally extending, radially spaced apart cables 68 that are slidably mounted in the flexible body portion 70 of the shaft 7. Using a suitable commercially available steering mechanism for shortening or lengthening the cables 68, the distribution head 8 can be made to point toward the right, left or up and down as directed by the physician to distribute the beam of ultraviolet light to various parts of the stomach as desired. The shaft 7 can be enclosed in a protective cover or sheath 74, e.g., polypropylene plastic that will slide easily through the esophagus 5a.

The ultraviolet light source 66 can comprise any suitable commercially available lighting source, e.g., a mercury vapor lamp. There are three classes of ultraviolet light: UVA (320 nanometers to 400 nanometers), UVB (290 nanometers to 320 nanometers), and UVC (200 nanometers to 290 nanometers). UVA can be provided from an incandescent source such as a tungsten, halogen or quartz iodide lamp. UVB can be provided by means of a suitable arc lamp such as a high pressure mercury lamp or a hot quartz lamp. UVC can be provided from an arc lamp using mercury vapor, a cold quartz lamp or a carbon arc lamp which mimics sunlight with a spectrum of from 280 nanometers to near infra-red. While any suitable ultraviolet light beam can be provided, it is preferred to use UVB or UVC light because of their greater effectiveness in killing or debilitating microorganisms through apoptosis.

To use the apparatus of FIGS. 6 and 7, the shaft 7 and head 8 are passed through the esophagus 5a conventionally with the balloon 20 in a collapsed position surrounding the head 8. After the head 8 is properly positioned in the stomach 5 under the control of the physician, the balloon 20 is inflated by passing a suitable fluid, e.g., air, through the inflation lumen 40 until the balloon 20 has expanded the stomach 5 at the desired location, thereby distending the rugae so that the pockets otherwise present are spread out evenly over the surface of the balloon 20. The light source 66 is then turned on, causing the UV light to pass through the fiber optic bundle 64 and out through the distribution head 8. The distribution head 8 and the balloon 20 can then be repositioned in the stomach as desired to expose all of the infected areas or, alternatively, the control cables 68 can be manipulated so as to point the head 8 toward the areas of the stomach that require treatment. Observations can be carried out by means of a viewing port and eyepiece 72 of known construction or through a separate endoscope (not shown) that is passed through the esophagus 5a into the stomach 5 alongside the flexible shaft 7.

In another form of the invention, the same apparatus is employed as already described in FIGS. 6 and 7, except that the light source 66 comprises a suitable commercially available infrared light source. The light source 66 can, for example, be an erbium laser, which is preferably operated intermittently and on low power compared to the power used for removing skin blemishes, scars, tattoos, etc., to enable the microorganisms to be killed without damaging the surrounding tissue.

Figure 8:
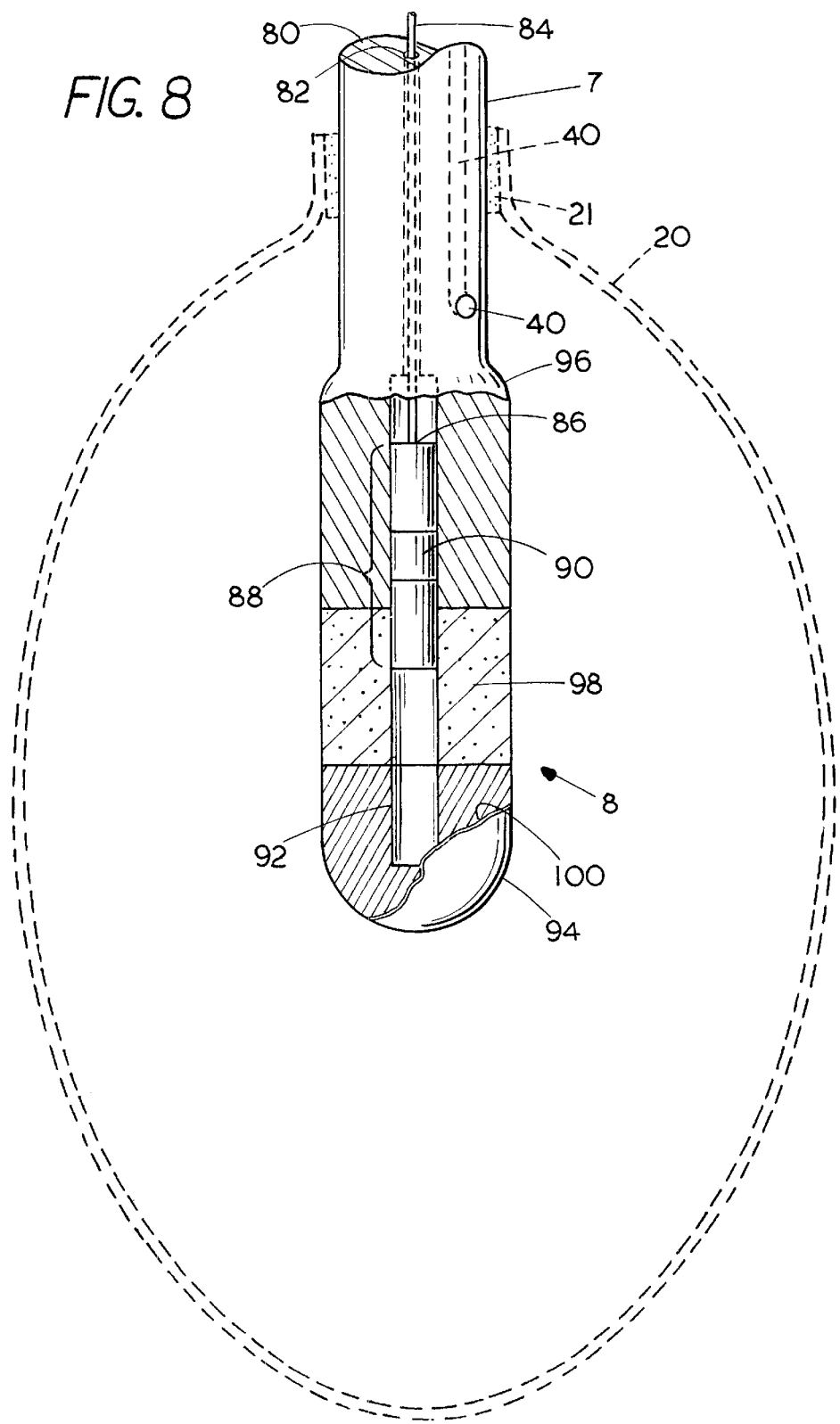
FIG. 8 is a cross-sectional view of the invention in use with a radioactive isotope employed for providing ionizing radiation.

Refer now to FIG. 8 which illustrates the use of the invention with radioactive isotopes to provide ionizing radiation for killing or debilitating *H. pylori* or other microorganisms through apoptosis. Radioactive isotopes provide the ionizing electromagnetic radiation through radioactive decay that can expose healthcare workers to radiation and require a shielded room. The present invention provides a way of shielding the isotope before and after use. In this case the flexible shaft 7 has a body portion 80 that is uniform throughout and contains a longitudinally extending lumen 82 in which a control cable 84 is slidably mounted. The distal end 86 of the control cable 84 is secured to a cylindrical slug 88 that is formed mostly of a shielding material such as lead but has a central portion 90 which is formed from a radioactive isotope. The slug 88 is slidably mounted in a bore 92 within the energy supply head 8 which includes two shielding portions including a distal portion 94 and a proximal portion 96, both formed of a suitable shielding material such as lead that is useful in shielding radioactive material. The shields 94, 96 are joined by an annular central portion 98 formed from a radiation-transparent material such as a suitable ceramic or plastic resinous material which allows radiation to be emitted when the slug 88 is moved under the direction of the physician distally so that the radioactive isotope 90 is exposed in the radiation transparent area 98 at the center of the distribution head 8. The distribution head 8 is enclosed in a sheath or coating of biocompatible material 100 such as polyethylene or Teflon®.

During use with the cable 84 pulled up, the shaft 7 and head 8 are inserted through the esophagus 5*a* into the stomach 5 conventionally, with the balloon 20 in a collapsed condition. Inflation fluid is then forced through the inflation lumen 40 into the balloon 20 to expand it sufficiently to spread out the walls of the stomach as described above. The cable 84 is then moved distally so as to shift the slug 88 containing the radioactive isotope 90 downwardly in FIG. 8 until the radioactive material 90 is aligned with the annular radiation-transparent wall 98, thereby allowing the ionizing radiation to pass from the radioactive isotope 90 radially in all directions from the head 8. After passing through the balloon 20, the radiation will strike the wall of the stomach 5 or other body cavity, killing or debilitating the *H. pylori* or other pathogenic microorganisms lining the wall of the cavity being treated. As treatment progresses, the balloon 20 and/or head 8 are repositioned under the control of the physician so as to redirect the ionizing radiation to the desired areas and for the length of time required to accomplish the required treatment. Because bacteria are much more sensitive to ionizing radiation than human tissue, the *H. pylori* and other bacteria can be killed or debilitated by apoptosis with little, if any, damage to the host tissue. As soon as the treatment is completed, the cable 84 is pulled, causing the slug 88 to slide proximally in the head 8 until the isotope 90 is completely surrounded by the lead shielding. The balloon 20 is then deflated and the instrument is withdrawn. As described above, the instrument shown in FIG. 8 can be positioned in any suitable manner, e.g., by observation through an endoscope (not shown) that is inserted through the esophagus alongside the shaft 7 into the stomach 5.

Any of the instruments 6 (including the shaft 7, head 8 and balloon 20) of FIGS. 1–8 can be inserted into the body cavity alone or, if desired, through the lumen of a commercially available endoscope of suitable known construction.

Isotopes emit ionizing radiation through the phenomenon of nuclear disintegration The ionizing radiation supplied by the isotope 90 can be either beta or gamma radiation. The beta radiation does not have the penetrating power of the gamma radiation, which will pass entirely through the body and into the room surrounding the patient, therefore requiring a radiation-shielded operating room. It is preferred that the ionizing radiation used have relatively shallow penetrating power, since there is usually no reason to go to any substantial depth. *H. pylori*, for example, is located on the surface of the epithelium lining the stomach. It is contemplated in accordance with the present invention to select the penetration depth of the ionizing radiation so that it penetrates only into the surface layer where the *H. pylori* is located, thereby protecting the patient from unnecessary radiation damage. For that reason, when an isotope is used to supply ionizing radiation, beta radiation is preferred to gamma radiation because of its reduced penetrating power.

In general, the use of non-radioactive sources is preferred to the radioactive source described in connection with FIG. 8, since the use of radioactive sources requires special handling, environmental considerations, and is subject to greater radiation danger. In the United States, only radiation oncologists can prescribe a therapy and dose involving radioactive isotopes. Moreover, gamma sources require a shielded catheterization laboratory. Because of the penetrating power of gamma radiation, the healthcare workers must leave the room while the patient is being treated. When gamma radiation is employed, the isotope 90 can comprise radioactive iridium-192 ($Ir^{192}$) which is available in the hospital because of its use in cancer treatment. Alternatively, a suitable beta radiation source such as potassium-32 or strontium-90 can be used as the isotope 90. Beta sources typically have a soft tissue penetration depth of less than one-half inch and therefore reduce the unwanted exposure of healthy tissue compared to gamma radiation. Beta sources are also easier to handle than gamma sources and pose a smaller risk to the patient and healthcare worker.

Radio waves and microwaves can also be used in accordance with the invention for destroying pathogenic microorganisms such a *H. pylori* in the lining of a body cavity. Microwave energy can be supplied to the distribution head 8 of the device shown in FIGS. 6 and 7 by removing the fiber optic bundle 64 to provide a hollow wave guide through the flexible shaft 7 for conveying microwave energy from a suitable magnetron at the source 66 to the radiant energy distribution head 8 where it is directed through the balloon 20 onto the walls of the body cavity surrounding the head 8. The microwave energy is preferably adjusted to heat the inner surface of the body cavity so as to preferentially kill bacteria and other microorganisms living at the surface or lining of the body cavity.

Radio wave energy can be provided using the apparatus of FIGS. 3 and 4, but without a vacuum in the tube 28 between the electrodes 16 and 18. Instead, a radio frequency field can be set up between the electrodes 16 and 18 to produce heating of the body tissue when the body tissue is placed adjacent to or between the electrodes. To provide the radio frequency field, a powerful RF oscillator can be applied across the electrodes 16 and 18 so as to heat the body tissue between them, as the body tissue acts as a dielectric of a capacitor in which dielectric losses cause heating within the tissue. The RF oscillator can, if desired, be followed by RF amplifier stages for generating high frequency currents that produce heat within the part of the body cavity that is being treated for destroying the pathogenic bacteria on or within the tissue. Other forms of radio wave energy known to those skilled in the art can also be used for destroying microorganisms. In this embodiment of the invention, the balloon 20 can be eliminated since it is generally desirable to position the tissue being treated against or between the electrodes 16 and 18.

All publications and patents are herein incorporated by reference to the same extent as if each individual publication or patent was specifically and individually indicated to be incorporated by reference.

Many variations of the present invention within the scope of the appended claims will be apparent to those skilled in the art once the principles described herein are understood.

What is claimed is:

1. A therapeutic method for denaturing or killing *Helicobacter pylori* within the body of a patient, said method comprising:
   providing a radiation source for inactivating the *H. pylon*,
   providing an elongated flexible shaft for transesophageal insertion into the stomach of the patient,
   providing a radiation distribution head at a distal end of the flexible shaft for supplying the radiation from the source to the stomach,
   producing x-ray radiation between an anode and a cathode located within the distribution head,
   inserting the distribution head into the stomach,
   causing the radiation to be transferred from the head to the epithelium of the stomach surrounding the head of the instrument in an amount sufficient to debilitate or kill *Helicobacter pylori* carried on the epithelium of the stomach.

2. The method of claim 1 wherein the distribution head is placed within a means for positioning the head equidistant from surrounding tissue.

3. The method of claim 2 wherein the means for positioning comprises an inflatable balloon having a free distal end spaced apart from the distribution head, and including inflating the balloon after inserting the distribution head into a body cavity of the patient to spread and flatten the walls of the body cavity and to maintain the distribution head a selected distance from the walls of the body cavity for enhancing uniform distribution of the radiation to the surrounding cavity walls.

4. A method of treating a gastrointestinal ailment of a patient comprising gastritis, gastric ulcer, duodenal ulcer, gastric cancer or gastric lymphoma resulting from an infectious disease produced by pathogenic microorganisms, said method comprising:
   providing a radiation source for inactivating pathogenic microorganisms within the gastrointestinal tract, said radiation source being adapted to kill or debilitate pathogenic microorganisms within the body of the patient by the application of the radiation upon the epithelium lining the wall of the body cavity without substantial damage, destruction or ablation of the body tissue of the patient,
   providing a radiation distribution head within the gastrointestinal tract for supplying the radiation in the range of about 200–320 nm from the source to a wall of the gastrointestinal tract,
   such that the penetration depth of the radiation enables the radiation to penetrate a surface portion of the gastrointestinal tract being treated where the pathogenic microorganisms are located,
   allowing the radiation to travel from the distribution head to the gastrointestinal tract wall while the head is within said tract so as to kill or debilitate the microorganisms thereon without substantial damage, ablation or destruction of the gastrointestinal tract of the patient to thereby improve or alleviate one or more of the symptoms of said gastrointestinal ailment.

5. The method of claim 4 wherein pressure is applied outwardly against an inner surface of the gastrointestinal tract to distend the gastrointestinal tract during the application of the ionizing radiation.

6. The method of claim 5 wherein the outward pressure is applied by inflating a balloon positioned around the distribution head to expand the balloon so as to distend the wall of the gastrointestinal tract and thereby smooth out the epithelium lining the gastrointestinal tract to enhance uniform treatment thereof.

7. The method of including inflating the balloon to a sufficient size to contact the wall of the gastrointestinal tract surrounding the balloon and centering the distribution head in the balloon so as to locate the distribution head substantially equidistant from the wall portion of the gastrointestinal tract in contact with the balloon.

8. The method of claim 4 including irradiating the gastrointestinal tract with ionizing radiation selected from the group consisting of x-ray radiation, beta radiation, gamma radiation, ultraviolet radiation, infra-red radiation, radio waves and microwaves.

9. The method of claim 4 wherein the patient suffers from stomach or duodenal ulcers and the pathogenic microorganism comprises *Helicobacter pylori*.

10. The method of claim 4 including positioning the distribution head as required to accomplish treatment of the stomach for debilitating or killing *Helicobacter pylori*, and repositioning the distribution head as required to treat different areas of the stomach until all of the infected areas in which treatment is desired are exposed to the ionizing radiation.

11. The method of claim 4 wherein the selected radiation penetrates only the surface portion of the gastrointestinal tract where the pathogenic microorganisms are located.

12. A therapeutic method for treating an infectious condition produced by pathogenic microorganisms within the body of a patient, said method comprising:
   providing an apparatus having a shaft for insertion into a body cavity of the patient and a radiation source for administering radiation to a lining of a body cavity of the patient which supports the pathogenic microorganisms,
   providing a radiation distribution head at a distal end of the shaft for supplying the radiation from the source to the lining of the body cavity,
   inserting the distribution head into a body cavity of the patient,
   causing the radiation in a range of from about 200 nm to 320 nm to be transferred from the head to the body cavity surrounding the head of the apparatus to debilitate or kill pathogenic microorganisms supported by the lining of the body cavity being treated with said radiation penetrating the surface layer where the pathogenic microorganisms are located, and
   debilitating or killing the pathogenic microorganisms thereby without substantial damage, destruction or ablation of the body tissue of the patient.

13. The method of claim 12 including the step of irradiating the body cavity with ionizing radiation selected from the group consisting of x-ray radiation, light radiation, beta radiation, gamma radiation, ultraviolet radiation, infrared radiation, radio waves, and microwaves.

14. The method of claim 12 wherein the body cavity comprises the gastrointestinal tract and the shaft and distribution head are inserted into the gastrointestinal tract of the patient for inactivating or destroying pathogenic microorganisms therein.

15. The method of claim 1 wherein the distribution head is repositioned in the body cavity to treat different areas of the body cavity until all of the infected areas in which treatment is desired are exposed to the ionizing radiation.

16. The method of claim 1 including the steps of:
   providing a balloon at the distribution head and
   introducing an inflation fluid into the balloon to expand the balloon so as to distend the wall of the body cavity and thereby smooth out the epithelium lining the body cavity for enhancing uniform treatment thereof.

* * * * *

UNITED STATES PATENT AND TRADEMARK OFFICE
CERTIFICATE OF CORRECTION

PATENT NO. : 6,464,625 B2
DATED : October 15, 2002
INVENTOR(S) : Robert A. Ganz

It is certified that error appears in the above-identified patent and that said Letters Patent is hereby corrected as shown below:

<u>Column 13,</u>
Line 5, cancel change "pylon" to -- pylori --
Line 62, cancel "ionizing"

<u>Column 14,</u>
Lines 8, 20, 47 and 59, cancel "ionizing"

Signed and Sealed this

Twenty-second Day of April, 2003

JAMES E. ROGAN
*Director of the United States Patent and Trademark Office*